United States Patent [19]

Zdrahala et al.

[11] Patent Number: 4,841,007
[45] Date of Patent: Jun. 20, 1989

[54] FLUORINATED POLYETHERURETHANES AND MEDICAL DEVICES THEREFROM

[75] Inventors: Richard J. Zdrahala, Dayton; Marc A. Strand, Centerville, both of Ohio

[73] Assignee: Becton Dickinson and Company, Franklin Lakes, N.J.

[21] Appl. No.: 173,892

[22] Filed: Mar. 28, 1988

[51] Int. Cl.⁴ .............................................. C08G 18/38
[52] U.S. Cl. ........................................ 528/28; 528/61; 528/65; 528/66
[58] Field of Search ..................... 528/28, 61, 65, 66

[56] References Cited

U.S. PATENT DOCUMENTS 4,098,742  7/1978  Mueller ................................ 528/70

Primary Examiner—Maurice J. Welsh
Attorney, Agent, or Firm—Richard E. Brown

[57] ABSTRACT

Non-blocking, hemocompatible, thermoplastic, fluorinated polyetherurethanes and a method for their preparation from fluorinated polyether glycols, isocyanates, chain extenders and a non-fluorinated polyol. The method includes two steps in which the fluorinated glycol is reacted initially with the diisocyanate to give a prepolymer having terminal isocyanate groups, and the prepolymer is then reacted with the extender and non-fluorinated polyol. Medical devices are fabricated from the fluorinated polyetherurethane.

11 Claims, No Drawings

FLUORINATED POLYETHERURETHANES AND MEDICAL DEVICES THEREFROM

BACKGROUND OF THE INVENTION

1. Field of the Invention

This invention relates to polyurethanes, and, more particularly relates to non-blocking thermoplastic polyurethanes, their preparation and their use in medical devices.

2. Background of the Invention

Thermoplastic polyurethanes to be used as elastomers and the like have been known for a long time. Products prepared from polyisocyanates, high molecular weight polyetherglycols, and low molecular weight diols and diamines as chain extenders are conventionally referred to as polyetherurethanes, and this term, abbreviated PEU, will be used in this disclosure for polyurethanes having a polyether backbone.

PEU compositions develop microdomains conventionally termed hard segment domains and soft segment domains. They are (AB)n type block copolymers, A being the hard segment and B the soft segment, and are occasionally termed as segmented polyurethanes. The hard segment domains form by localization of the portions of the copolymer molecules which include the isocyanate and extender components whereas the soft segment domains form from the polyether glycol portions of the copolymer chains. The hard segments are generally more crystalline and hydrophilic than the soft segments and these characteristics prevail, in general, for the respective domains. One disadvantage of polyurethane resins of the softness desired for many medical devices, e.g., resins having Shore A hardness less than abut 100, is surface blocking (tack) after extrusion or molding into desired shapes. To avoid this problem, many remedies have been developed in the art including the use of external mold release agents and the use of various antiblockers or detackifiers in admixture with the polymer. Most antiblocking agents/detackifiers are low molecular weight materials which have a tendency to migrate or leach out of the polymer. This represents a problem when the polyurethanes are to be used as biomaterials (tubing, prostheses, implants, etc.). The presence of such low molecular weight extractables can affect the biocompatibility of the polyurethanes and lead to surface degradation, such as fissuring or stress cracking.

Although not related to biomaterials, U.S. Pat. No. 4,057,595 to Rauner et al. discloses a method for modifying the physical characteristics of polyurethane elastomers to reduce blocking wherein the polyurethane contains, within the polymer chain, a siloxane-polyoxyalkylene block copolymer.

Soft, non-blocking thermoplastic polyoxyalkylene polyurethanes having up to 15% of a soft segment formed from a polysiloxane devoid of oxygen atoms bonded to both silicon and carbon are disclosed by Zdrahala et al. in U.S. Pat. No. 4,647,643.

Fluorine containing polyurethanes are known. Kato et al., in *Progress in Artificial Organs*, 1983, page 858, discloses polyurethanes synthesized from fluorinated isocyanates. Yoon et al., in Macromolecules 19, 1068 (1986) discloses polyurethanes synthesized from fluorinated chain extenders. Field et al., in U.S. Pat. No. 4,157,358 discloses a randomly fluorinated epoxyurethane resin.

Although some progress has been made toward providing a thermoplastic polyurethane which is non-blocking without additives, which provides a desirable balance of stiffness in air and softness in liquid and which is suitable for blood contact, further improvement is needed. This invention is directed toward fulfillment of this need.

SUMMARY OF THE INVENTION

One aspect of the present invention is a substantially non-blocking fluorinated polyetherurethane (hereinafter referred to as FPEU) having a hard segment content from about 20 to 70% which is prepared from a diisocyanate, a fluorinated polyol and a chain extender. Preferred FPEUs additionally contain in the soft segment a non-fluorinated polyether polyol. In the most preferred FPEUs of the invention, the hard segment contains 4,4'-diphenylmethane-diisocyanate (MDI) and 1,4-butanediol (BDO) as the extender and the soft segment contains a fluorinated polyether glycol (FPG) and polytetramethyleneether glycol (PTMEG).

Another aspect of the invention is a method to prepare the FPEUs of the invention. The method includes two steps. In the first step, all of the diisocyanate required for the polymer formulation is reacted with the FPG to give a quasi prepolymer mixed with excess diisocyanate. The quasi prepolymer is then reacted with a mixture of the additional polyol and the extender to give the FPEU.

In still another aspect of the invention, the FPEU is shaped into a medical article which may serve as a medical device or as part of a medical device contemplated to come into contact with blood. Preferred medical devices are grafts, prostheses and catheters, although other devices are clearly within the purview of the present invention.

The FPEUs of the invention are non-blocking and of high hydrolytic and oxidative stability. They have an excellent balance of physical and mechanical properties. In particular, they are hemocompatible and therefore useful for fabrication of medical devices, such as grafts, vascular prostheses and catheters to be used in contact with blood. (In the present disclosure, the term hemocompatible describes a surface that does not induce significant thrombosis or changes in blood cells, enzymes or electrolytes, does not damage adjacent tissue, and does not cause adverse immune responses or toxic reactions.)

The importance of using a flexible catheter to avoid damage to the blood vessel walls is well documented. Stiff catheters can cause thrombus generation and mechanically induced phlebitis. Catheters which are placed over-the-needle, nevertheless, must have some stiffness for ease of insertion. Long-line catheters also must have an optimum degree of flexibility for insertion and placement in tortuous vessels and yet have an appropriate degree of stiffness for kink resistance.

When used in a catheter, the FPEUs of the invention have sufficient stiffness for ease of insertion into a blood vessel, and, once inserted, soften sufficiently and in a controllable fashion on contact with the blood to facilitate advancement of the catheter through a tortuous path until the final desired position is reached.

DETAILED DESCRIPTION

While this invention is satisfied by embodiments in many different forms, there will herein be described in detail preferred embodiments of the invention, with the understanding that the present disclosure is to be considered as exemplary of the principles of the invention and is not intended to limit the invention to the embodiments described. The scope of the invention will be measured by the appended claims and their equivalents.

The present invention provides FPEUs which are substantially non-blocking, soften significantly under physiological conditions, and have good mechanical properties over a wide range of material hardnesses. This combination of properties, combined with excellent hemocompatibility, makes them particularly attractive for fabrication of medical devices to be used in contact with blood.

The FPEUs of the invention include three essential components, a diisocyanate, an FPG and a chain extender. Preferred compositions also include a non-fluorinated polyol, such as a polyalkyleneoxide polyol (PAO).

Suitable diisocyanates are aromatic diisocyanates such as MDI, 3,3'-diphenylmethane-diisocyanate, alicyclic diisocyanates such as isophorone diisocyanate and 4-4'-dicyclohexylmethane-diisocyanate, and aliphatic diisocyanates, as, for example, hexamethylene diisocyanate. The most preferred diisocyanate is MDI.

A quantity of diisocyanate from about 0.95 to 1.10 equivalents relative to the total equivalents of hydroxyl groups in the chain extender and the two polyol components may be used. Preferably, a slight excess of diisocyanate, as, for example 1.02 equivalents per equivalent of hydroxyl groups may be used.

Any polyether glycol having from about 20-70% fluorine by weight may serve as the FPG. Preferred FPGs have from about 30-60% by weight of fluorine in pendant perfluoroalkyl groups and are of the following general formula:

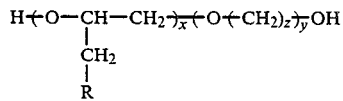

wherein R may be a perfluorinated alkyl group having from about 1 to 12 carbon atoms, x may be from about 1 to 4, Y may be from about 0 to 20 and Z may be from about 2 to 5. In preferred FPGs, R may be from about 4-10 carbon atoms. Most preferably, R is a perfluorohexyl group. Fluorinated polyols of the invention are available from E. I. DuPont de Nemours Co., Wilmington, Delaware.

the PAO included in the preferred compositions of the invention may be, for example, polyethylene glycol, polypropylene glycol, PTMEG and the like of mixtures thereof. Preferred polyols are PTMEG having a molecular weight of from about 500 to about 5000. The most preferred PAO is a PTMEG having a molecular weight of about 1000 or 2000. Such polyols are commercially available from DuPont as Terathane 1000 and 2000 respectively.

In addition to the PAO and FPG, additional polyols may be included in the FPEU of the invention. The additional polyol may be a polyether-polysiloxane glycol (PAO-PS). These well-known compounds are copolymers having polysiloxane units and polyalkylene oxide units. A preferred PAO-PS has a polydimethylsiloxane unit with polyalkylene oxide caps such as DC TM Q4-3667 fluid available from Dow Corning, Midland, MI.

Polyester glycols may also be included in the FPEUs of the invention. Exemplary of suitable polyester glycols are polyethylene adipate and polycaprolactone.

The chain extender may be a low molecular weight branched or unbranched diol, diamine or amino alcohol of up to 12 carbon atoms or mixtures thereof. Representative non-limiting examples of chain extenders are BDO; ethylene glycol; diethylene glycol; triethylene glycol; 1,2-propanediol; 1,3-propanediol; 1,6-hexanediol (HDO); 1,4-bishydroxymethyl cyclohexane, hydroquinone, dihydroxyethyl ether, ethanolamine, ethylenediamine and hexamethylenediamine. Preferred chain extenders are BDO and HDO.

The FPEU of the invention may have from about 20 to 70% by weight of hard segment preferably about 25 to 45 percent. The PFG may be from about 1 to 100, preferably about 5 to 35 percent by weight of the soft segment. As is well known to those skilled in the art, suitable proportions of the components may readily be calculated from the pre-selected hard segment content so that any desired hardness from about Shore 50 A to 80 D may be obtained.

The FPEU of the invention may be prepared by the conventional two step or prepolymer method, or preferably, by a quasi prepolymer procedure. In the conventional prepolymer method, the polyols may be reacted with a stoichiometric amount of diisocyanate so that each hydroxyl group of the polyols is reacted with an isocyanate group giving a prepolymer having isocyanate terminal groups (a process conventionally referred to as capping). The prepolymer molecules may then be further chain extended by reaction between their terminal isocyanate groups and the chain extender.

In the preferred quasi prepolymer method of the invention, the FPG is reacted alone with the diisocyanate. This approach ensures full incorporation of the fluorinated polyol into the quasi prepolymer, as described below. The isocyanate groups of the quasi prepolymer may then be further reacted with the PAO and extender.

As can be seen from the general structure above, the preferred FPG is a polyalkylene oxide glycol having pendant perfluoroalkyl groups and a secondary hydroxyl group. As is well known in the art, secondary hydroxyl groups are, in general, less reactive than primary hydroxyl groups. Accordingly, in the most preferred prepolymer method of the invention, the FPG is reacted with the diisocyanate under conditions which favor capping of both hydroxyl groups of the FPG. In general, this may be accomplished by slow addition of the FPG to the diisocyanate whereby the diisocyanate is always present in large excess. The general procedure for the quasi prepolymer technique is given in Example I. It is evident, however, that various modifications of this procedure may be readily appreciated by those skilled in the art.

When the FPEU of the invention is to be used for fabrication of medical devices contemplated to come into contact with a body fluid, it is preferred to carry out the above-described procedure in the absence of a catalyst. However, in some cases, the use of a conventional catalyst may be advantageous. Any catalyst as known in the art may be used, such as stannous octoate or dibutyl tin dilaurate. The catalyst may be used in about 0.001% to 0.5% percent by weight of the reactants.

Depending on the intended use, other components may be incorporated into the PEU composition of the invention in order to achieve particular properties. For example additives such as flow aids, flatting agents, plasticizers, polymerization inhibitors, heat stabilizers and surface cure modifiers may be added to the formulation prior to prepolymer formation, prior to conversion of the prepolymer to the FPEU or preferably after completion of FPEU formation. Such additives and their use to modify polymer properties are conventional and well known to those skilled in the art.

Representative FPEUs ranging in hard segment content from 25 to 56% prepared in accordance with Example I are listed in Table I. The products of Table I were prepared with an FPG having a fluorine content of 45%.

about 90°. Lack of blocking is also associated with the low surface energy consequent to the fluorine atoms in the soft segment. In contrast, the receding contact angles, which are related to the more hydrophilic hard segment, are virtually unchanged (about 55° for both control and inventive polyurethanes) as expected, since fluorine atoms are not present in the hard segment.

Evaluation of the softening characteristics of the FPEUs of the invention may be carried out (Example II) by the procedure of Zdrahala et al., *Materials Research Society Symposium Proceedings*, 55,407 (1986). The results are given in Table II and show that at 5% tensile modulus, the percentage of softening ranges from 10.3 to 45.9 and at 25% tensile modulus, the per-

TABLE I

| FPEU NO. | MDI WT. % | POLYOL, WEIGHT PERCENTAGE | | | | EXTENDER WEIGHT % | | HARD SEGMENT WT. % | HARDNESS | |
|---|---|---|---|---|---|---|---|---|---|---|
| | | PTMEG 1000 | PTMEG 2000 | FPG | PAO-PS | BDO | HDO | | A | D |
| 1 | 29.72 | 50 | | 14.86 | 0 | 5.43 | | 35.14 | 82 | 38 |
| 2 | 28.52 | | 50 | 14.26 | 0 | 7.21 | | 35.74 | 88 | 44 |
| 3 | 28.84 | 50 | | 14.42 | 0 | | 6.74 | 35.58 | 80 | 35 |
| 4 | 27.36 | | 50 | 13.86 | 0 | | 8.95 | 36.32 | 85 | 42 |
| 5 | 22.24 | 55 | | 15.0 | 5.0 | 2.76 | | 25.0 | 62 | |
| 6 | 29.72 | 50 | | 15.0 | 5.0 | | 4.73 | 30.0 | 73 | |
| 7 | 28.30 | 45 | | 15.0 | 5.0 | | 6.70 | 35.0 | 81 | |
| 8 | 33.96 | 54 | | 5.0 | 0 | 7.04 | | 41.0 | | 53 |
| 9 | 33.02 | 49 | | 10.0 | 0 | 7.18 | | 41.0 | | 48 |
| 10 | 33.67 | 44 | | 15.0 | 0 | 7.33 | | 41.0 | | 49 |
| 11 | 44.07 | 39 | | 5.0 | 0 | 11.30 | | 56.0 | | 67 |
| 12 | 43.93 | 34 | | 10.0 | 0 | 12.07 | | 56.0 | | 67 |
| 13 | 43.79 | 29 | | 15.0 | 0 | 12.22 | | 56.0 | | 67 |
| Control PEU 1 | 34.11 | 59 | | 0 | 0 | 6.90 | | 41.0 | | 51 |
| Control PEU 2 | 44.22 | 44 | | 0 | 0 | 11.78 | | 56.0 | | 65 |

The FPEUs of the invention may be tested for their physical-mechanical properties and surface energetics by well known methods (Example II). Observed data are given in Table II.

In general, the FPEUs of the invention exhibit essentially the same desirable balance of tensile strength, flexibility, elongation, modulus and tear strength as conventional non-fluorinated thermoplastic polyetherurethanes (control PEUs). The presence of the fluorine atoms, however, render the products of the invention substantially non-blocking, even when soft, in contrast to the significant tack characteristic of control PEUs. The non-blocking feature of the FPEUs of the invention is readily evident to the touch or qualitatively demonstrated by maintaining the FPEU surface in contact with another surface for a period of time and observing that the surfaces do not substantially adhere when separated. Non-blocking is associated with their enhanced surface hydrophobicity characterized by high advancing contact angles, which range from about 105° to 125°. The advancing contact angles for control PEUs is centage of softening ranges from 32.8 to 56.4. Comparison of the softening percentages shown by the FPEUs of the invention with control PEUs (Table II) show that the fluorine atoms had little effect on the known excellent softening characteristics of PEUs (Zdrahala et al. (*Thermoplastic Polyurethanes, Materials for Vascular Catheters*, in Polyurethanes in Biomedical Engineering II, H. Planck et al., eds. Elsevier Science Publishers B. V. Amsterdam, Netherlands, 1987, p. 1).

Hemocompatibility may be determined by monitoring both platelet and fibrinogen deposition using an ex vivo canine A/V shunt model, as described by Zdrahala et al. (supra.). FPEUs having only PAO and FPG in the polyol component are comparable or slightly better in platelet deposition to control PEUs. Incorporation of a PAO-PS into the soft segment increased fibrinogen deposition. However, even though fibrinogen is a precursor of fibrin, the "skeleton" of thrombus, no increase in platelet deposition was seen for FPEUs containing PAO-PS.

TABLE II

| FPEU | TENSILE MODULUS PSI | | | | TENSILE PSI | ULTIMATE ELONGATION PERCENTAGE | DIE C TEAR PLI | SOFTENING PERCENTAGE | |
|---|---|---|---|---|---|---|---|---|---|
| | 5% | 25% | 100% | 200% | | | | 5% TS | 25% TS |
| 1 | 106 | 409 | 752 | 1,178 | 4,445 | 423 | 257 | 14.2 | 32.8 |
| 2 | 241 | 719 | 1,163 | 1,859 | 4,667 | 368 | 209 | 25.7 | 37.6 |
| 3 | 109 | 398 | 653 | 930 | 7,224 | 602 | 343 | 22.0 | 33.7 |
| 4 | 170 | 544 | 881 | 1,371 | 7,096 | 503 | 314 | 25.9 | 38.4 |
| 5 | 37 | 112 | 181 | 221 | 1,286 | 1,298 | 131 | 45.9 | 56.4 |
| 6 | 83 | 281 | 475 | 660 | 5,875 | 648 | 225 | 14.5 | 34.2 |
| 7 | 78 | 350 | 571 | 770 | 4,982 | 748 | 322 | 10.3 | 32.9 |
| 8 | 172 | 675 | 1,079 | 1,720 | 9,819 | 478 | 278 | 20.9 | 39.7 |
| 9 | 196 | 684 | 1,074 | 1,784 | 8,751 | 478 | 337 | 25.0 | 42.1 |
| 10 | 213 | 729 | 1,181 | 2,039 | 8,303 | 466 | 296 | 24.4 | 46.4 |

TABLE II-continued

| FPEU | TENSILE MODULUS PSI | | | | TENSILE PSI | ULTIMATE ELONGATION PERCENTAGE | DIE C TEAR PLI | SOFTENING PERCENTAGE | |
|---|---|---|---|---|---|---|---|---|---|
| | 5% | 25% | 100% | 200% | | | | 5% TS | 25% TS |
| 11 | 809 | 1,821 | 2,775 | 4,630 | 9,445 | 390 | 609 | 37.8 | 39.7 |
| 12 | 966 | 2,043 | 2,871 | 4,396 | 4,910 | 257 | 599 | 38.6 | 42.3 |
| 13 | 1,096 | 2,191 | 3,019 | 5,065 | 4,297 | 220 | 526 | 18.2 | 32.8 |
| Control PEU 1 | 161 | 611 | 975 | 1,531 | 9,686 | 506 | 324 | 19.9 | 35.5 |
| Control PEU 2 | 701 | 1,571 | 2,394 | 4,026 | 7,123 | 347 | 536 | 47.3 | 42.5 |

Because of their excellent hemocompatibility, the FPEUs of the invention are useful materials for fabrication of medical devices. Preferred devices are shaped articles to be used in contact with blood. Exemplary of medical devices contemplated to fall within the scope of the present invention are tubing, valves, artificial hearts, membranes, and most preferably, catheters, grafts and vascular prosthesis.

The following examples are provided to further illustrate the invention, but are not to be considered in any way as limitative of the invention.

EXAMPLE I

A quantity of FPG having an average molecular weight of 1867 and a fluorine content of 45% was dried by vacuum-stripping at 55°-60° C. and 5-10 mm Hg for 1 hour. A quantity of MDI was vacuum filtered to remove impurities. The remainder of the polymer intermediates, PTMEG with an average molecular weight of 1000 and BDO, were mixed in the appropriate amounts and vacuum-stripped at 55°-60° C. and 5-10 mm Hg for 30 minutes.

The FPG (111.4 g) was added dropwise to the continuously stirred MDI (222.9 g) at 55°-60° C. After the addition was complete (1 hour) the mixture was stirred under vacuum (5-10 mm Hg) for an additional 2 hours. The resultant modified prepolymer was then added to the mixture of PTMEG (375.0 g) and BDO (40.7 g). The entire system was vigorously stirred until the reaction temperature reached 80° C. and the viscosity of the reaction product began to significantly increase. The polymer was poured onto a TEFLON ® lined tray and cured for one hour at 125° C. followed by a 24 hour post-cure at ambient conditions. The resultant solid polymer had a Shore A durometer hardness of 82 (FPEU#1). The polymer was chipped, forced air dried to less than 0.05% moisture and extruded as given in Example II.

EXAMPLE II

Polymer Evaluation

A. Bulk

Polymer hardness was evaluated on the Shore A and D scales. The results are given in Table I.

B. Extrusion

Extrusion conditions were predicted from melt viscosity measurements (Siegloff-McKelvey Capillary Rheometer). Ribbons (10 mil), tubing (3 mm ID) and rods (16 gauge) were extruded with a Brabender Plasti-Corder ® extruder having a ¾ inch screw and standard dies.

C. Physical Properties

Tensile properties were measured on samples (ribbons or pressed films) that were equilibrated at 23° C. and 50% relative humidity, seven days after extrusion, using an Instron Model 1122 Universal Testing Machine with a 50 lb. load cell. Tensile strength, elongation and modulus were determined by ATM procedure D638, and Die C and slit tear strengths were determined by ASTM procedures D1004 and D1938 respectively. Results are given in Table II.

D. Dynamic Contact Angles

Dynamic contact angles were measured using a Wilhelmy plate type Wet-Tek ® instrument manufactured by Cann Instruments, Inc., Cerritos, CA. Samples were cut (1 cm×3 cm) from pressed films or extruded ribbons and washed with hexane to remove surface contaminants. The samples were equilibrated for 24 hours at room temperature and 52% relative humidity. Advancing and receding dynamic contact angles were measured in distilled H$_2$O for six different samples and averaged. Sample annealing was done at 125° C. for 15 minutes where applicable.

E. Softening

Softening was determined on extruded ribbon samples after immersion for two hours in N-saline at 37° C. Percent softening was calculated as the percent change in the initial value of the 5% and 25% tensile moduli(TS).

What is claimed is:

1. A thermoplastic polyetherurethane consisting substantially of a product from the reaction of a diisocyanate, a fluorinated polyol, a nonfluorinated polyol selected from the group consisting of a polyalkyleneoxide polyol and a polyester polyol and a chain extender of 2 to 12 carbon atoms selected from the group consisting of a diol, diamine and amino alcohol.

2. The polyetherurethane of claim 1 wherein said diisocyanate is selected from the group consisting of 4,4'-diphenylmethane-diisocyanate, 3,3'-diphenylmethane-diisocyanate, 4,4'-dicyclohexyl-methane-diisocyanate, isophorone diisocyanate and hexamethylene diisocyanate.

3. The polyetherurethane of claim 1 wherein said fluorinated polyol is selected from the group having the formula

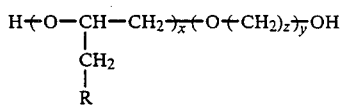

wherein R is a perfluorinated alkyl group having about 1 to 12 carbon atoms, x is about 1 to 4, Y is about 0 to 20 and Z is about 2 to 5.

4. The polyetherurethane of claim 1 wherein said polyalkyleneoxide polyol is polytetramethylene ether glycol.

5. The polyetherurethane of claim 1 wherein said chain extender is selected from the group consisting of 1,4-butanediol, ethylene glycol; diethylene glycol; triethylene glycol; 1,2-propanediol; 1,3-propanediol; 1,6-hexanediol; 1,4-bis-hydroxymethyl cyclohexane, hydroquinone, dihydroxyethyl ether, ethanolamine, ethylenediamine and hexamethyl- enediamine.

6. A thermoplastic polyetherurethane consisting substantially of a product from the reaction of a diisocyanate, a fluorinated polyol and a chain extender of 2 to 12 carbon atoms selected from the group consisting of a diol, diamine and amino alcohol.

7. A thermoplastic polyetherurethane consisting substantially of a product from the reaction of 4,4'-diphenylmethane-diisocyanate, a fluorinated polyether polyol, polytetramethylenether glycol and a chain extending diol of 2 to 6 carbon atoms.

8. A method for preparing a thermoplastic polyetherurethane consisting substantially of:
reacting a fluorinated polyol with a diisocyanate to give a prepolymer having isocyanate terminal groups; and
reacting said isocyanate terminal groups with a chain extender of 2 to 12 carbon atoms selected from the group consisting of a diol, diamine and amino alcohol.

9. The method in accordance with claim 8 wherein said isocyanate terminal groups are further reacted with a nonfluorinated polyol selected from the group consisting of a polyalkyleneoxide polyol and a polyester polyol.

10. The method of claim 8 wherein said fluorinatd polyol is selected from the group having the formula

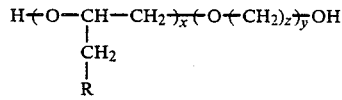

wherein R is a perfluorinated alkyl group having about 1 to 12 carbon atoms, x is about 1 to 4, Y is about 0 to 20 and Z is about 2 to 5.

11. A method for preparing a thermoplastic polyetherurethane consisting substantially of reacting a fluorinated polyether polyol with 4,4'-diphenylmethane-diisocyanate to give a prepolymer having isocyanate terminal groups and reacting said terminal groups with a polytetramethylene ether glycol and a chain extending diol of 2 to 6 carbon atoms.

* * * * *